United States Patent
Venkataraman

(10) Patent No.: US 11,594,325 B2
(45) Date of Patent: Feb. 28, 2023

(54) METHOD AND SYSTEM FOR AUTOMATICALLY TRACKING AND MANAGING INVENTORY OF SURGICAL TOOLS IN OPERATING ROOMS

(71) Applicant: Verb Surgical Inc., Santa Clara, CA (US)

(72) Inventor: Jagadish Venkataraman, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 120 days.

(21) Appl. No.: 16/894,018

(22) Filed: Jun. 5, 2020

(65) Prior Publication Data

US 2020/0303065 A1   Sep. 24, 2020

Related U.S. Application Data

(63) Continuation of application No. 16/129,607, filed on Sep. 12, 2018, now Pat. No. 10,679,743.

(51) Int. Cl.
| | | |
|---|---|---|
| G16H 40/20 | (2018.01) | |
| G06Q 10/08 | (2023.01) | |
| G16H 40/40 | (2018.01) | |

(52) U.S. Cl.
CPC .............. *G16H 40/20* (2018.01); *G06Q 10/08* (2013.01); *G16H 40/40* (2018.01)

(58) Field of Classification Search
CPC ........ G16H 40/63; G16H 40/20; G16H 40/40; G06Q 10/08; G06K 9/00718; G06K 9/00765

(Continued)

(56) References Cited

U.S. PATENT DOCUMENTS 3,706,184 A   12/1972   Tucker et al.
6,920,347 B2   7/2005   Simon
(Continued)

FOREIGN PATENT DOCUMENTS

EP           2420197         2/2012
KR    10-2008-0001622        1/2008
(Continued)

OTHER PUBLICATIONS

International Preliminary Report on Patentability for International Application No. PCT/US2018/051562 dated Mar. 25, 2021, 7 pages.

(Continued)

*Primary Examiner* — Andrew Joseph Rudy
(74) *Attorney, Agent, or Firm* — Womble Bond Dickinson (US) LLP

(57) ABSTRACT

Embodiments described herein provide various examples of automatically processing surgical videos to detect surgical tools and tool-related events, and extract surgical-tool usage information. In one aspect, a process for automatically tracking usages of robotic surgery tools is disclosed. This process can begin by receiving a surgical video captured during a robotic surgery. The process then processes the surgical video to detect a surgical tool in the surgical video. Next, the process determines whether the detected surgical tool has been engaged in the robotic surgery. If so, the process further determines whether the detected surgical tool is engaged for a first time in the robotic surgery. If the detected surgical tool is engaged for the first time, the process subsequently increments a total-engagement count of the detected surgical tool. Otherwise, the process continues monitoring the detected surgical tool in the surgical video.

20 Claims, 5 Drawing Sheets

(58) Field of Classification Search
USPC .......................................................... 705/28
See application file for complete search history.

(56) References Cited

U.S. PATENT DOCUMENTS

| | | | |
|---|---|---|---|
| 7,068,842 B2 | 6/2006 | Liang et al. | |
| 7,317,955 B2 | 1/2008 | McGreevy | |
| 7,379,790 B2* | 5/2008 | Toth | ........................ A61B 34/32 |
| | | | 901/33 |
| 7,840,042 B2 | 11/2010 | Kriveshko et al. | |
| 7,853,305 B2 | 12/2010 | Simon et al. | |
| 8,086,008 B2 | 12/2011 | Coste-Maniere et al. | |
| 8,108,072 B2* | 1/2012 | Zhao | ........................ A61B 34/30 |
| | | | 700/250 |
| 8,131,031 B2 | 3/2012 | Lloyd | |
| 8,147,503 B2* | 4/2012 | Zhao | ........................ A61B 34/37 |
| | | | 382/128 |
| 8,504,136 B1 | 8/2013 | Sun et al. | |
| 8,527,094 B2 | 9/2013 | Kumar et al. | |
| 8,600,551 B2 | 12/2013 | Itkowitz et al. | |
| 9,026,247 B2* | 5/2015 | White | ........................ A61B 34/20 |
| | | | 700/250 |
| 9,215,293 B2 | 12/2015 | Miller | |
| 9,413,976 B2* | 8/2016 | DiCarlo | ................. A61B 34/30 |
| 10,126,219 B2* | 11/2018 | Shabram | .................. G01N 3/08 |
| 10,588,699 B2* | 3/2020 | Richmond | ............. A61B 34/37 |
| 10,803,320 B2* | 10/2020 | Calmus | .................. G06V 20/52 |
| 11,081,229 B2* | 8/2021 | Alvi | ..................... A61B 90/361 |
| 11,176,945 B2* | 11/2021 | Paul | ........................ G16H 40/63 |
| 11,189,379 B2* | 11/2021 | Giataganas | ............. G06F 3/017 |
| 11,202,676 B2* | 12/2021 | Lightcap | ................ A61B 19/50 |
| 11,205,508 B2 | 12/2021 | Venkataraman et al. | |
| 2003/0208196 A1 | 11/2003 | Stone | |
| 2005/0251156 A1 | 11/2005 | Toth et al. | |
| 2010/0285438 A1 | 11/2010 | Kesvadas et al. | |
| 2011/0301447 A1 | 12/2011 | Park et al. | |
| 2012/0253360 A1 | 10/2012 | White et al. | |
| 2014/0286533 A1 | 9/2014 | Luo et al. | |
| 2015/0005622 A1* | 1/2015 | Zhao | ..................... A61B 34/30 |
| | | | 382/103 |
| 2015/0230875 A1 | 8/2015 | Shademan et al. | |
| 2016/0140875 A1 | 5/2016 | Kumar et al. | |
| 2016/0166345 A1 | 6/2016 | Kumar et al. | |
| 2018/0357514 A1 | 12/2018 | Zisimopoulos et al. | |
| 2021/0000461 A1* | 1/2021 | Charles | .................. G16H 20/40 |
| 2021/0290317 A1* | 9/2021 | Sen | ...................... G06N 3/0472 |

FOREIGN PATENT DOCUMENTS

| | | |
|---|---|---|
| KR | 20140126322 | * 10/2014 |
| WO | 2017075541 | 5/2017 |

OTHER PUBLICATIONS

Extended European Search Report for European Application No. 18920011.6 dated Feb. 3, 2022, 10 pages.

Lin, Henry C., et al., "Towards automatic skill evaluation: Detection and segmentation of robot-assisted surgical motions," Computer Aided Surgery, vol. 11, No. 5, Dec. 31, 2006, pp. 220-230.

Padoy, Nicolas, "Workflow and Activity Modeling for Monitoring Surgical Procedures," HAL archvies-ouvertes.fr, retrieved from the Internet <http://www.theses.fr/2010NAN10025/document, Apr. 14, 2010, 166 pages.

Loukas, C., "Video content analysis of surgical procedures," Surg. Endosc. 32, 554-568 (2018). https://doi.org/10.1007j 500464-017-5878-1, Received: Feb. 14, 2017 / Accepted: Sep. 7, 2017 / Published online: Oct. 26, 2017 (c) Springer Science + Business Media, LLC 2017 (Year: 2017).

Extended European Search Report for European Application No. 18933279.4 dated May 17, 2022, 9 pages.

* cited by examiner

METHOD AND SYSTEM FOR AUTOMATICALLY TRACKING AND MANAGING INVENTORY OF SURGICAL TOOLS IN OPERATING ROOMS

PRIORITY CLAIM AND RELATED PATENT APPLICATIONS

This patent application is a continuation of, and hereby claims the benefit of priority under 35 U.S.C. § 120 to co-pending U.S. patent application Ser. No. 16/129,607, filed on 12 Sep. 2018, entitled, "Method and Apparatus for Automatically Tracking and Managing Inventory of Surgical Tools in Operating Rooms," by inventor Jagadish Venkataraman. The above-listed application is hereby incorporated by reference as a part of this patent document.

TECHNICAL FIELD

The present disclosure generally relates to building surgical video analysis tools and, more specifically, to systems, devices and techniques for automatically segmenting surgical videos, detecting surgical tools and tool-related events, and extracting surgical-tool usage information to guide or make recommendations to the surgeons.

BACKGROUND

Tracking the use and managing the inventory of surgical tools in the operating rooms (ORs) play a highly important role in improving surgical outcomes and delivering quality patient care. For example, certain surgical tools have limited shelf life in terms of the number of times they can be fired. Hence, it is necessary to track and record the usages of these surgical tools. Currently, tracking and recording the usages of surgical tools in the ORs involve the surgical staff manually performing these tasks using either a computer or by making a note on the whiteboard. As another example, for minimally invasive procedures (MIS) such as a laparoscopy surgery, it is useful to detect which tools are engaged for tool inventory purposes. Today, information regarding which tools are engaged during a surgical procedure is also collected manually by the surgical staff. In fact, most of the surgical tool-related metrics in the ORs are collected manually by the surgical staff. Unfortunately, manually counting or tracking surgical-tool-related metrics for each and every surgical procedure is highly labor-intensive and error-prone.

SUMMARY

Embodiments described herein provide various examples of a surgical-tool-management system for automatically processing surgical videos to detect surgical tools and tool-related events, and extract surgical-tool usage information to guide or make recommendations to surgical staff. In one aspect, a process for automatically tracking usages of robotic surgery tools is disclosed. This process can begin by receiving a surgical video captured during a robotic surgery. The process then processes the surgical video to detect a surgical tool in the surgical video. Next, the process determines whether the detected surgical tool has been engaged in the robotic surgery. If so, the process further determines whether the detected surgical tool is engaged for a first time in the robotic surgery. If the detected surgical tool is engaged for the first time, the process subsequently increments a total-engagement count of the detected surgical tool. Otherwise, the process continues monitoring the detected surgical tool in the surgical video.

In some embodiments, processing the surgical video to detect the surgical tool includes applying a machine-learning model on a set of video images in the surgical video, wherein the machine-learning model is trained to detect and identify a set of surgical tools associated with the robotic surgery.

In some embodiments, the process determines whether the detected surgical tool has been engaged in the robotic surgery by first determining if the detected surgical tool continues to present in the surgical video for at least a predetermined minimum time period. If so, the process determines that the surgical tool has been engaged in the robotic surgery. Otherwise, the process continues monitoring the surgical tool in the surgical video.

In some embodiments, prior to determining whether the detected surgical tool has been engaged in the robotic surgery, the process determines, for each type of a set of surgical tool types, a minimum time period required to engage the surgical tool type in a surgical procedure.

In some embodiments, if the detected surgical tool has been previously engaged in the robotic surgery, the process continues monitoring other surgical tools in the robotic surgery.

In some embodiments, after incrementing the total-engagement count of the detected surgical tool, the process records the updated engagement count of the detected surgical tool for tool inventory purposes.

In some embodiments, if the updated engagement count has reached a maximum number of engagements for the safe and/or effective use of the detected surgical tool, the process marks the detected surgical tool as expired.

In some embodiments, after determining that the detected surgical tool has been engaged in the robotic surgery, the process activates a tool-usage counting process to track and record a number of uses of the detected surgical tool during the tool engagement.

In some embodiments, the tool-usage counting process tracks the number of uses of the detected surgical tool by using a second machine-learning model trained to detect an event in the surgical video representing a single use of the detected surgical tool.

In some embodiments, the detected surgical tool is a surgical stapler, and the second machine-learning model is trained to detect a single firing of the surgical stapler each time a firing knob of the surgical stapler is pushed from a first position to a second position.

In some embodiments, the detected surgical tool is an electrocautery tool, and the second machine-learning model is trained to detect a single firing of the electrocautery tool each time a plume of surgical smoke is detected.

In some embodiments, the process can further receive an existing number of total uses of the detected surgical tool from previous engagements of the detected surgical tool. The process subsequently updates the total uses of the detected surgical tool by combining the recorded number of uses during the tool engagement with the existing number of total uses from the previous engagements.

In some embodiments, the process further includes the steps of: determining if a maximum number of total uses of the detected surgical tool has been reached; and if so, generating a tool-expiration notification to be communicated to surgical staff.

In another aspect, an apparatus for automatically tracking usages of robotic surgery tools is disclosed. This apparatus includes one or more processors and a memory coupled to the one or more processors. The memory stores instructions that, when executed by the one or more processors, cause the apparatus to: receive a surgical video captured during a robotic surgery; process the surgical video to detect a surgical tool in the surgical video; determine whether the detected surgical tool has been engaged in the robotic surgery; and if so, further determine if the detected surgical tool has been previously-engaged in the robotic surgery. If the detected surgical tool has not been previously-engaged in the robotic surgery, the memory stores instructions that, when executed by the one or more processors, cause the apparatus to increment a total-engagement count of the detected surgical tool. Otherwise, the memory stores instructions that, when executed by the one or more processors, cause the apparatus to continue monitoring the detected surgical tool in surgical video.

In some embodiments, the memory further stores instructions that, when executed by the one or more processors, cause the apparatus to activate a tool-usage counting process to track and record a number of uses of the detected surgical tool during the tool engagement after determining that the detected surgical tool has been engaged.

In some embodiments, the memory further stores instructions that, when executed by the one or more processors, cause the apparatus to use a second machine-learning model to track the number of uses of the detected surgical tool, wherein the second machine-learning model is trained to detect an event in the surgical video representing a single use of the detected surgical tool.

In some embodiments, the memory further stores instructions that, when executed by the one or more processors, cause the apparatus to: receive an existing number of total uses of the detected surgical tool from previous engagements of the detected surgical tool; and update the total uses of the detected surgical tool by combining the recorded number of uses during the tool engagement with the existing number of total uses from the previous engagements.

In some embodiments, the memory further stores instructions that, when executed by the one or more processors, cause the apparatus to: determine if a maximum number of total uses of the detected surgical tool has been reached; and if so, generate a tool-expiration notification to be communicated to surgical staff.

In yet another aspect, a robotic surgical system is disclosed. This robotic surgical system includes: one or more surgical tools each coupled to a respective robotic arm; an endoscope configured to capture surgical videos; and a controller coupled to each robotic arm and the endoscope. The controller is configured to: receive a surgical video captured by the endoscope during a robotic surgery; process the surgical video to detect a surgical tool in the surgical video; determine whether the detected surgical tool has been engaged in the robotic surgery; and if so, further determine whether the detected surgical tool is engaged for a first time in the robotic surgery: if so, increment a total-engagement count of the detected surgical tool; otherwise, continue monitoring the detected surgical tool in the surgical video.

In some embodiments, the controller is further configured to: detect that the total-engagement count has reached a maximum number of engagements for the safe and/or effective use of the detected surgical tool and subsequently mark the detected surgical tool as expired and update a status of the detected surgical tool for tool inventory purposes.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1:
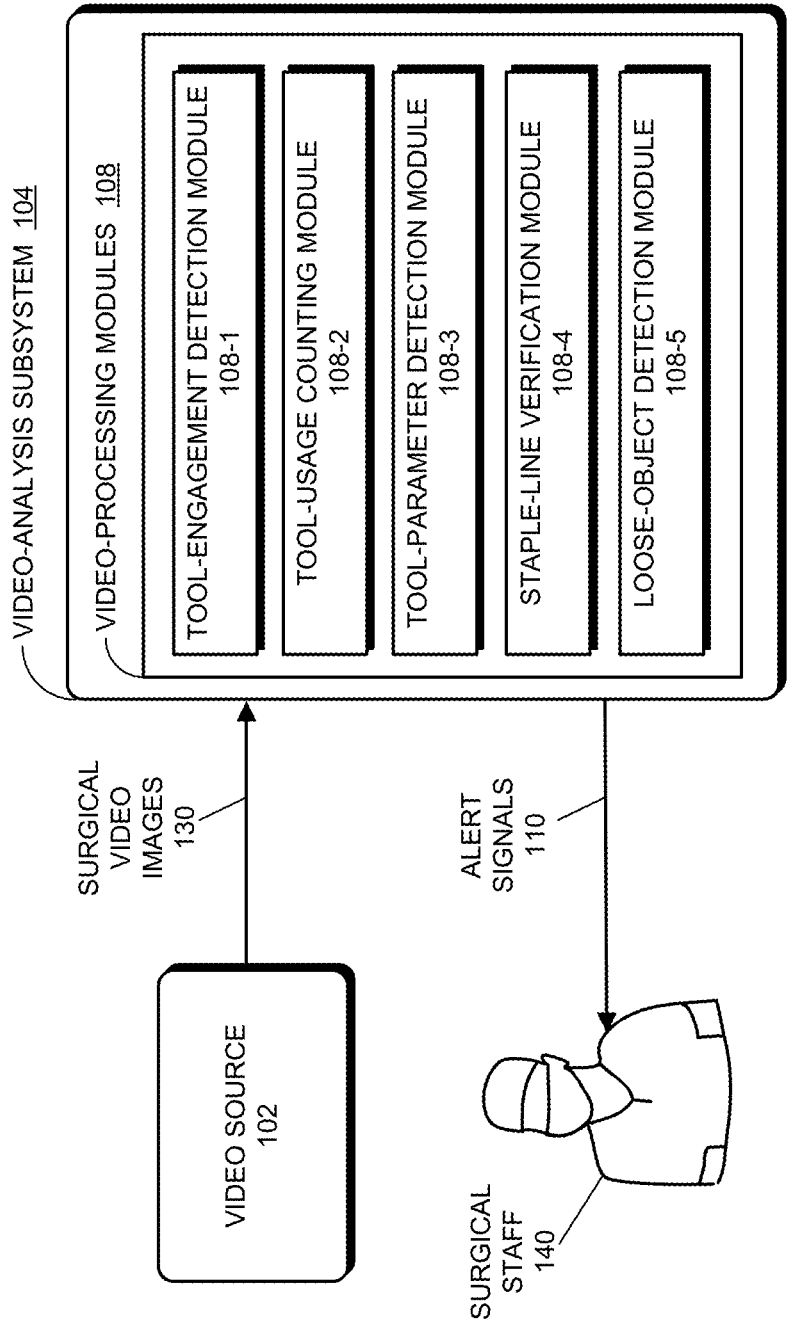
FIG. 1 shows a block diagram of an exemplary surgical-tool-management system 100 in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures that involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exists and continues to be created as a result of a large number of surgical cases performed by many different surgeons from different hospitals. The simple fact of the existence of a huge (and constantly increasing) number of surgical videos of a particular surgical procedure makes processing and analyzing the surgical videos of the given procedure a potential machine-learning problem.

This patent disclosure provides various examples of applying machine-learning-based and/or computer-vision-based techniques to automatically perform various surgical tool-related tasks, such as tool detection, tool usage counting and tracking, and outcome analysis, and to automatically generate alerts/guidance to the surgical staff. The disclosed automated techniques relieve surgical staff from manually performing the above tasks, thereby freeing up the valuable time of surgical staff for other more important tasks, easing the surgical workflow, and improving surgical outcomes by eliminating manual errors.

In various embodiments, the tool-related data can be mined from all types of surgical video feeds, including but not limited to open surgery videos, endoscopic surgery videos, and robotic surgery videos. For each type of tool-related data, data can be mined from such videos using various machine-learning-based techniques, conventional computer-vision techniques such as image processing, or a combination of machine-learning and Computer-vision techniques.

FIG. 1 shows a block diagram of an exemplary surgical-tool-management system 100 in accordance with some embodiments described herein. As can be seen in FIG. 1, surgical-tool-management system 100 includes at least a video source 102 and a video-analysis subsystem 104. In some embodiments, video source 102 can include live surgical procedure videos. In these embodiments, video source 102 can be coupled to or part of a live video capturing module configured to capture and record real-time surgical procedure videos and/or still images during live surgical procedures. Moreover, this live video capturing module can be coupled to or part of a surgical platform, such as an open surgery platform, an endoscopic surgery platform, or a robotic surgery platform. As such, video source 102 can generate and provide various types of surgical videos, including but not limited to open surgery videos, endoscopic surgery videos, and robotic surgery videos. In some embodiments, video source 102 can include stored/archived surgical procedure videos. In these embodiments, video source 102 can be coupled to or part of a storage system or device that stores previously captured surgical procedure videos and/or still images. As such, video source 102 can store and provide various types of surgical videos, including but not limited to open surgery videos, endoscopic surgery videos, and robotic surgery videos.

As can be seen in FIG. 1, video-analysis subsystem 104 is coupled to video source 102 and configured to receive live or stored surgical videos and/or still images (collectively referred to as "surgical video images 130" hereinafter) from video source 102 and perform various surgical video analyses to extract tool-related information. More specifically, video-analysis subsystem 104 includes a set of video-processing modules 108, wherein each of the set of video-processing modules 108 can be used to process surgical video images 130 to extract one or more particular types of tool-related information.

For example, video-processing modules 108 can include a tool-engagement detection module 108-1 for processing surgical video images 130 and detecting which surgical tools have been engaged during a recorded surgical procedure. In various embodiments, tool-engagement detection module 108-1 can include a machine-learning or a computer-vision technique trained to detect and identify various surgical tools. Tool-engagement detection module 108-1 can employ this machine-learning or computer-vision technique to detect various surgical tools captured in surgical video images 130. Hence, tool-engagement detection module 108-1 operates to automatically identify different types of tool engagements captured in surgical video images 130 and automatically generate an inventory of the detected tools involved in the associated surgical procedure.

Video-processing modules 108 can include a tool-usage counting module 108-2 for processing surgical video images 130 to determine how many times a particular surgical tool has been fired or used in another manner. Note that certain surgical tools, such as surgical staplers or some power-based surgical tools (e.g., electrocautery tools), have limited uses in terms of the number of times they can be fired or engaged/used in other manners. For example, a given surgical stapler or a given electrocautery tool can only be fired a limited number of times before the tool has to be replaced. As a result, it is highly desirable to keep track of the number of firings/uses/applications of a given surgical tool having limited use Such a surgical tool having limited use is also referred to as a "limited-use surgical tool" hereinafter. Conventionally, this usage data is tracked manually by surgical staff for certain surgical procedures, such as endoscopic procedures. In various embodiments, tool-usage counting module 108-2 can include a machine-learning or a computer-vision technique trained to identify and keep track of each time a given surgical tool is fired. Tool-usage counting module 108-2 can employ this machine-learning or computer-vision technique to automatically identify each time a given limited-use surgical tool is fired or used in another manner, thereby keeping track of the usage of the given surgical tool. For example, for a surgical stapler, a machine-learning model can be trained to detect each time a firing knob of the surgical stapler is pushed from a first position to a second position to detect a single firing of the surgical stapler. As another example, for a powered cautery tool, a machine-learning model can be trained to detect each time a plume of surgical smoke is generated as a single firing of the cautery tool. Note that this usage information is accumulative and tool-usage counting module 108-2 can combine the usage information extracted from surgical video images 130 from multiple surgical videos.

In some embodiments, when a maximum usage (e.g., the maximum number of firings of a surgical stapler) is determined to have been reached, tool-usage counting module 108-2 can generate an alert or a notification to be communicated to surgical staff (described in more detail below). In some embodiments, tool-usage counting module 108-2 can also be used to count events such as the number of staple cartridges used or the number of sponges used. Hence, tool-usage counting module 108-2 operates to automatically determine how many times a particular surgical tool has been used or the number of time a given type of surgical item has been applied without requiring human intervention or manual processing to eliminate human errors.

In some embodiments, tool-usage counting module 108-2 can be configured to infer a length of the tissue traversed by a surgical tool. For example, based on the determined number of uses of a surgical tool, such as a surgical stapler, and a length of the surgical tool, tool-usage counting module 108-2 can quickly estimate the approximate length of a tissue that the surgical tool has traversed along the tissue. By combining the automatic tool-usage counting and the length estimate, the approximate length of the tissue that the surgical tool has traversed can be quickly estimated without the need to manually measure the traversed length.

Video-processing modules 108 can also include a tool-parameter detection module 108-3 for processing surgical video images 130 to determine a given parameter associated with a given surgical tool. For example, the color of the surgical stapler cartridge/load is an important parameter to collect because different colors of the cartridge/load represent different types of staples for different tissue thicknesses. The color of the cartridge/load is also an important parameter during a post-operation summary procedure to summarize what types of stapler cartridge/load have been used on the patient during the procedure. Conventionally, the color of the cartridge/load is tracked visually and manually by surgical staff. Some future surgical stapler designs aim to transmit the color information as a feedback signal through the surgical stapler.

In various embodiments, tool-parameter detection module 108-3 can include a machine-learning or a computer-vision model trained to identify the color of each surgical stapler load. Tool-parameter detection module 108-3 can employ this machine-learning or computer-vision model to automatically identify the color of each surgical stapler load captured in surgical video images 130, thereby greatly simplifying the color identification/tracking process without the need to make a design change for the surgical stapler tool just to collect the color information.

Video-processing modules 108 can also include a staple-line verification module 108-4 for processing surgical video images 130 to verify stability and uniformity of each staple line formed in a tissue or a body part. Note that malformed staple lines can result in leakage, especially when multiple malformed staples group or align in a certain geometrical pattern. Staple-line verification module 108-4 can include a machine-learning or a computer-vision model trained to identify malformed staples and compute their relative geometry. Staple-line verification module 108-4 can employ this machine-learning or computer-vision model to automatically process surgical video images 130 including the formed staple lines and to identify malformed staples and determine their relative geometry. This determined geometry of malformed staples can then be used to predict a probability of leakage.

Video-processing modules 108 can also include a loose-object detection module 108-5 for processing surgical video images 130 to identity loose or floating objects such as loose or open staples in the tissue. During the operation of a surgical stapler, the knife in the stapler that cuts through a tissue between two rows of formed staple lines can sometimes accidentally cut through one of the already formed staple lines resulting in "crotch staples," i.e., loose, V-shaped staples that can later float around in the patient's body. If not removed, these loose staples have the ability to move around, puncture other tissues and cause bleeding. In various embodiments, loose-object detection module 108-5 can include a machine-learning or a computer-vision model trained to identify "crotch staples" or other forms of loose staples. Loose-object detection module 108-5 can employ this machine-learning or computer-vision model to automatically process surgical video images 130 of the formed staple lines and to identify "crotch staples" and other forms of loose staples. This determined geometry of malformed staples can then be used to predict potential leaks. In some embodiments, when loose staples are detected, loose-object detection module 108-5 can generate an alert or a notification to be communicated to surgical staff (described in more detail below). The surgical staff can then take proper action to remove these loose staples, thus avoiding potential injuries.

Note that various video-processing modules 108-1 to 108-5 are just some examples of surgical-video-processing modules for automatic surgical-tool management. It can be understood that, over time, video-processing modules 108 can include an increasingly large number of modules to automatically process video images and extract even more types of surgical-tool-related information.

As illustrated in FIG. 1, video-processing modules 108 can generate alert signals 110 to surgical staff 140 in real time. Surgical staff 140 can then take proper action based on the nature of alert signals 110. For example, when a maximum usage of a surgical tool is detected, tool-usage counting module 108-2 can generate an alert signal 110 to alert surgical staff 140. Surgical staff 140 can then replace the old surgical tool with a new surgical tool. In some embodiments, alert signals 110 can also directly trigger the surgical tool to be locked from further operation.

Detection of Tool Engagement with the Tool-Engagement Detection Module

Conventionally, tracking surgical tool engagements during a surgical procedure requires the surgical staff to visually track each new tool engagement and log information into a PC or make notes on the whiteboard. Using machine-learning, computer-vision, or a combined technique of machine-learning and computer-vision, a computer can be programmed or trained to detect the occurrences and subsequently identify the tool type for different tools in the surgical videos. The proposed tool-engagement detection module 108-1 can process surgical videos and detect which surgical tools have been engaged during a recorded surgical procedure.

In some embodiments, the video processing outputs from the disclosed tool-engagement detection module can be corroborated with feedback data collected directly from the surgical systems. For example, in some robotic surgery systems, each time a surgical tool is mounted on a robotic arm, the tool information, such as tool type and tool ID, can be obtained through an interface of the robotic arm, and this tool information can be logged and stored. In some embodiments, tool information collected by the surgical robot can be combined with the tool detection output of the disclosed tool-engagement detection module to provide a more complete record for each detected tool engagement, and for more accurate tool tracking.

Figure 2:
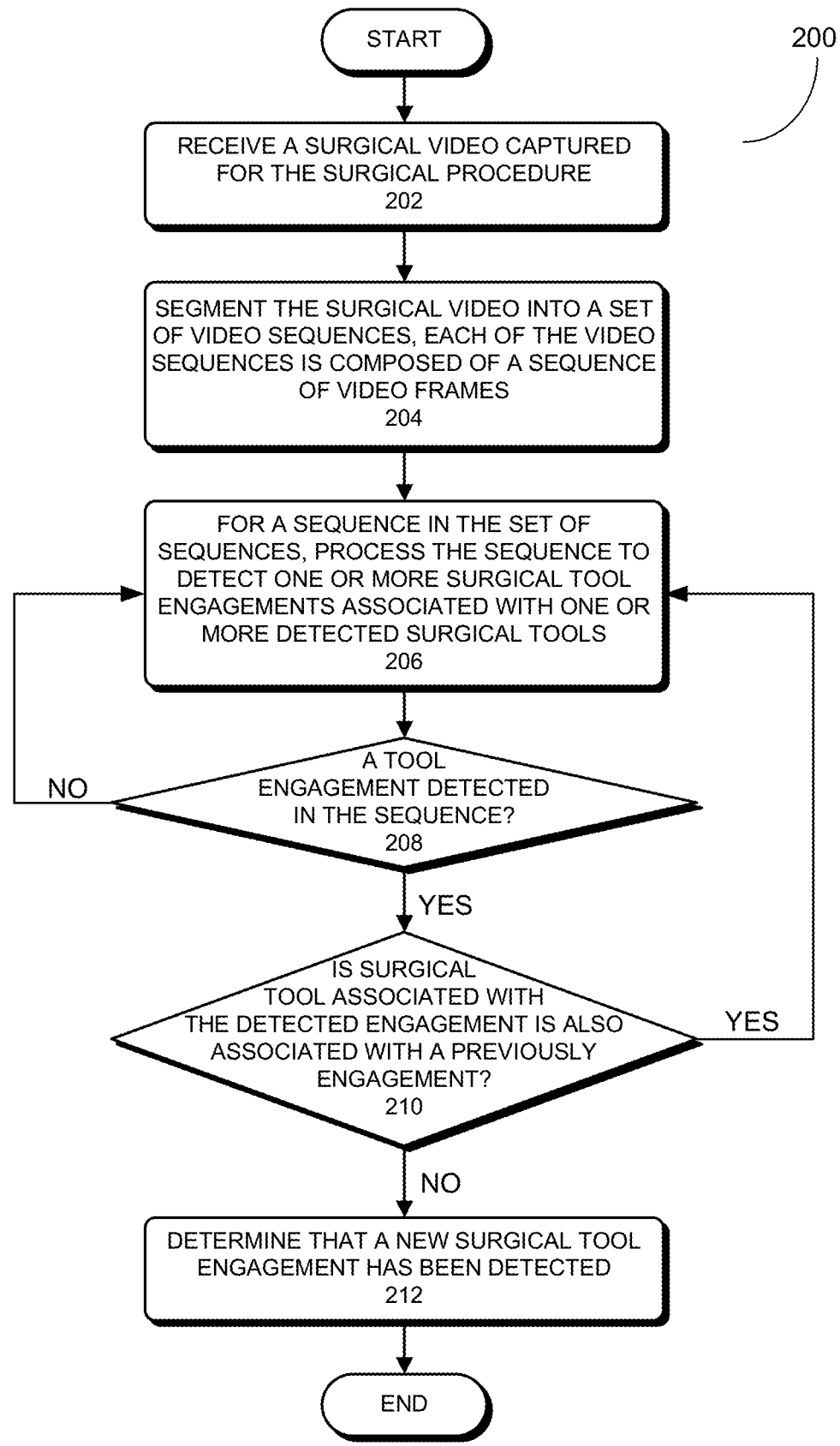
FIG. 2 presents a flowchart illustrating an exemplary process for processing a surgical video to detect a new surgical tool engagement during a recorded surgical procedure in accordance with some embodiments described herein.

FIG. 2 presents a flowchart illustrating an exemplary process 200 for processing a surgical video to detect a new surgical tool engagement during a recorded surgical procedure in accordance with some embodiments described herein. In one or more embodiments, one or more of the steps in FIG. 2 may be omitted, repeated, and/or performed in a different order. Accordingly, the specific arrangement of steps shown in FIG. 2 should not be construed as limiting the scope of the technique. Note that process 200 can be implemented within the above-described tool-engagement detection module 108-1.

Process 200 begins by receiving a surgical video captured for the surgical procedure (step 202). Note that the surgical video can be an open surgery video, an endoscopic surgery video, or a robotic surgery video. Next, process 200 segments the surgical video into a set of video sequences, wherein each of the video sequences is composed of a sequence of video frames (step 204). For example, process 200 can first segment the surgical video into a set of surgical phases, and further segment a given surgical phase in the set of surgical phases into a set of surgical subphases or surgical tasks. More detail of segmenting a surgical video into phases, subphases and/or tasks is described in a related patent application entitled "Machine-Learning-Oriented Surgical Video Analysis System," having Ser. No. 15/987,782, and filing date of 23 May 2018, the content of which is incorporated herein by reference. In some embodiments, each of the segmented surgical phases, subphases, and tasks can be further segmented into a set of equal-length video sequences, wherein each of the sequences includes a predetermined number of video frames.

For each sequence of video frames in the set of video sequences, process 200 then processes the sequence of video frames to detect one or more surgical tool engagements associated with one or more detected surgical tools in the sequence of video frames (step 206). In some embodiments, to detect a tool engagement, process 200 first detects a surgical tool in the sequence of video frames using a machine-learning model trained to detect and identify a set of surgical tools. For example, the machine-learning model can be trained to detect and identify each of a set of required surgical tools for a given surgical procedure captured by the surgical video. In various embodiments, this machine-learning model can include a regression model, a deep neural network-based model, a support vector machine, a decision tree, a Naive Bayes classifier, a Bayesian network, or a k-nearest neighbors (KNN) model. In some embodiments, this machine-learning model is constructed based on a convolutional neural network (CNN) architecture, an recurrent neural network (RNN) architecture, or another form of deep neural network (DNN) architecture.

Note that processing multiple consecutive video frames to detect a surgical tool engagement can be more accurate than processing a single video frame. This is because a meaningful engagement of a surgical tool is often associated with a minimum time period. Hence, when a surgical tool appears in the video for a time period shorter than the minimum time period, the surgical tool may not be actually engaged but simply presented for a different reason in the video. For example, if a surgical stapler appears in a sequence of video frames for less than a second then disappears, the surgical stapler is usually not engaged during the short appearance. Note that this minimum time period can be measured by a predetermined number of consecutive video frames. Hence, in some embodiments, after a surgical tool is detected in the sequence of video frames being processed, the detected surgical tool is determined to be a tool engagement only when the surgical tool remains being detected for the predetermined number of consecutive video frames. Those skilled in the art will appreciate that this minimum time period can vary significantly for different types of surgical tools. Therefore, after a given surgical tool has been detected, a corresponding minimum time period for the given surgical tool will be applied to determine if the given surgical tool is actually engaged. Note that because the recorded number of engagements of a given surgical tool is directly related to calculating the remaining shelf life/number-of-uses of the given surgical tool, it is necessary to distinguish actual tool engagements from accidental appearances of the given surgical tool.

At step 208, process 200 determines if a surgical tool engagement has been detected. If not, process 200 terminates or returns to step 206 to process the next sequence of video frames in the set of video sequences. If a surgical tool engagement is detected in the current sequence of video frames, process 200 then determines if the detected surgical tool associated with the detected tool engagement is associated with a previously identified surgical tool engagement in a previously-processed sequence of video frames in the set of video sequences (step 210). If so, process 200 terminates or returns to step 206 to process the next sequence of video frames in the set of video sequences. However, if the detected surgical tool engagement has not been detected in the previously-processed sequences of video frames, process 200 determines that a new surgical tool engagement has been detected and subsequently records the detected tool engagement for tool inventory purposes (step 212).

Note that the above-described process of taking tool inventory regarding which surgical tools have been engaged during a surgical procedure can be combined with a tool-usage counting process to track the number of times a given surgical tool has been used. More specifically, for a given surgical tool with limited use, each time the surgical tool is detected and associated with a newly-identified surgical tool engagement, the tool-usage counting process can be activated to track and record the number of individual uses/applications of the given surgical tool to tissues during the newly-identified tool engagement. Note that for the given surgical tool with limited use, the usage counting is accumulative over each newly-identified engagement and previously-identified engagements of the given surgical tool, if any. In some embodiments, when the accumulative number of uses of the given surgical tool has reached a predetermined number of uses (e.g., the maximum number of effective uses or the maximum number of safe uses), the given surgical tool is considered expired and a replacement warning for the given surgical tool can be issued to the surgical staff. An exemplary process of tracking a total number of times a given surgical tool has been used is described below in conjunction with FIG. 3.

Counting Tool Usage with the Tool-Usage Counting Module

As mentioned above, certain surgical tools, such as a surgical stapler, have limited uses in terms of the number of times they can be fired or used in other manners. Conventionally, this usage data is tracked visually and manually by surgical staff for certain surgical procedures, such as endoscopic procedures. Using machine-learning, computer-vision, or a combined technique of machine-learning and computer-vision, a computer can be programmed or trained to identify and keep track of each time a target surgical tool is fired or used in another manner. The disclosed tool-usage counting module 108-2 can use model-based techniques to process surgical videos and identify and keep track of each time a target surgical tool is fired or used in another manner in each new application.

In some embodiments, the video processing outputs from the disclosed tool-usage counting module can be corroborated with feedback data collected directly from the surgical systems. For example, in some robotic surgery systems, each time a surgical tool is mounted on a robotic arm, the tool information, such as tool type and tool ID can be obtained through an interface of the robotic arm, and this tool information can be logged and stored. In these embodiments, tool information collected by the surgical robots can be processed to determine the number of times a target surgical tool has been mounted on one or more surgical robots. This data can then be combined with the tool tracking output from the disclosed tool-usage counting module 108-2 for the same surgical tool to provide a more accurate usage count for the surgical tool.

Figure 3:
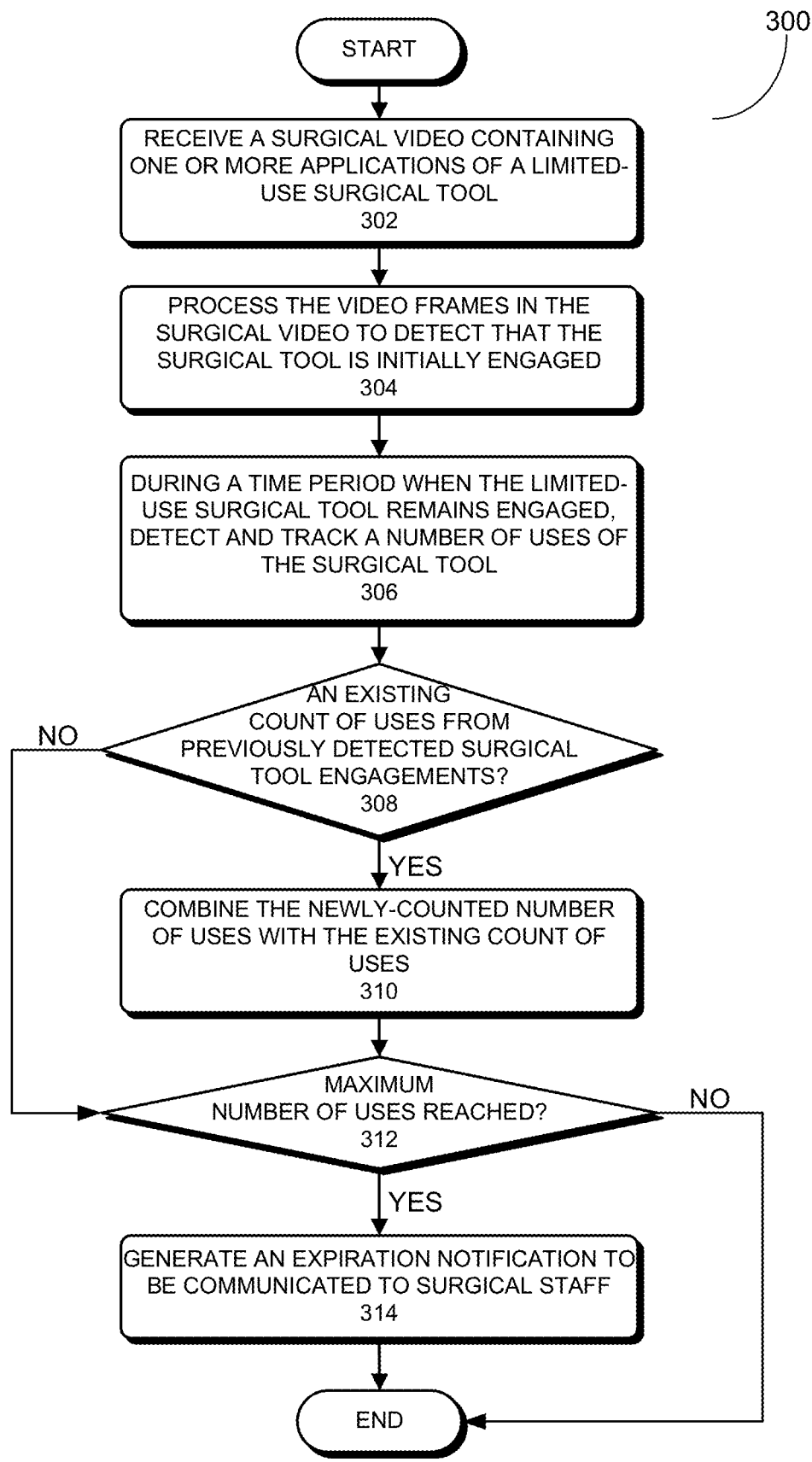
FIG. 3 presents a flowchart illustrating an exemplary process for processing a surgical video to track a number of uses of a limited-use surgical tool in accordance with some embodiments described herein.

FIG. 3 presents a flowchart illustrating an exemplary process 300 for processing a surgical video to track a number of uses of a limited-use surgical tool in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique. Note that process 300 can be implemented within the above-described tool-usage counting module 108-2. Note that a limited-use surgical tool described herein can include a surgical stapler, a power-based cautery tool, or some other power-based surgical tools.

Process 300 begins by receiving a surgical video containing one or more applications of a limited-use surgical tool to tissues (step 302). Note that the surgical video can be an open surgery video, an endoscopic surgery video, or a robotic surgery video. Process 300 then processes the video frames in the surgical video to detect that the limited-use surgical tool is initially engaged (step 304). For example, a trained machine-learning model based on a set of images of the limited-use surgical tool as training data can be used to detect and identify a limited-use surgical tool in step 304. In various embodiments, this machine-learning model can include a regression model, a deep neural network-based model, a support vector machine, a decision tree, a Naive Bayes classifier, a Bayesian network, or a k-nearest neighbors (KNN) model. In some embodiments, this machine-learning model is constructed based on a CNN architecture, an RNN architecture, or another form of DNN architecture. Note that during a surgical procedure captured in the surgical video, there can exist multiple engagements of the same limited-use surgical tool separated by other surgical tasks. Hence, step 304 should be interpreted as detecting each new engagement of the limited-use surgical tool rather than just the very first engagement of the limited-use surgical tool in the surgical video.

Next, during a time period when the detected limited-use surgical tool remains engaged, process 300 detects and tracks a number of uses of the limited-use surgical tool (step 306). For example, after an engagement of the limited-use surgical tool was initially detected, a machine-learning model for detecting a single use of the limited-use surgical tool can be activated. In some embodiments, for a surgical stapler, this machine-learning model can be trained to detect each time a firing knob of the surgical stapler is pushed from a first position to a second position, which can be counted as a single use. As another example, for a powered cautery tool, this machine-learning model can be trained to detect each time a plume of surgical smoke is generated as a single use of the cautery tool. Note that, an operation which is considered as a single use for one type of limited-use surgical tool can be significantly different from an operation which is considered as a single use for another type of limited-use surgical tool.

After determining the number of uses of the limited-use surgical tool during the current surgical tool engagement, the process next determines if there is an existing count of uses of the limited-use surgical tool from the previously detected surgical tool engagements in the surgical video (step 308). If so, process 300 combines the newly-counted number of uses of the limited-use surgical tool during the current engagement with the existing count of uses of the limited-use surgical tool (step 310). In some embodiments, if the limited-use surgical tool operates within a robotic surgery system, then the limited-use surgical tool is installed onto a robot arm of the robotic surgery system when the limited-use surgical tool is being used. In these embodiments, the existing count of uses of the limited-use surgical tool can be stored in a storage device, such as a tool memory of the robotic surgery system. Hence, when the limited-use surgical tool is initially engaged with the robot arm, tool information such as tool ID, the existing count of uses of the limited-use surgical tool can be read off of the tool memory by a tool controller of the robotic surgery system. Next, after the total number of uses of the limited-use surgical tool has been updated with the newly-counted number of uses, the updated total number of uses of the limited-use surgical tool can be written back into the tool memory of the robotic surgery system by the tool controller to replace the existing count of uses of the limited-use surgical tool.

After updating the total number of uses of the limited-use surgical tool, process 300 next determines if a maximum number of uses of the limited-use surgical tool has been reached (step 312). For example, the maximum number of uses of a surgical stapler can be determined based on a statistical number of effective uses of a surgical stapler before the surgical stapler becomes unstable. In the robotic surgery system example, the maximum number of uses of the tool can also be stored in the tool memory of the robotic surgery system and retrieved from the memory by the tool controller to be used by process 300 to execute step 312. In some embodiments, once the maximum number of uses is reached, the limited-use surgical tool can be considered as expired, and process 300 generates an expiration alert or notification to be communicated to the surgical staff (step 314). Otherwise, process 300 terminates or returns to step 304 to continue tracking the uses of the same limited-use surgical tool (not shown).

Figure 4:
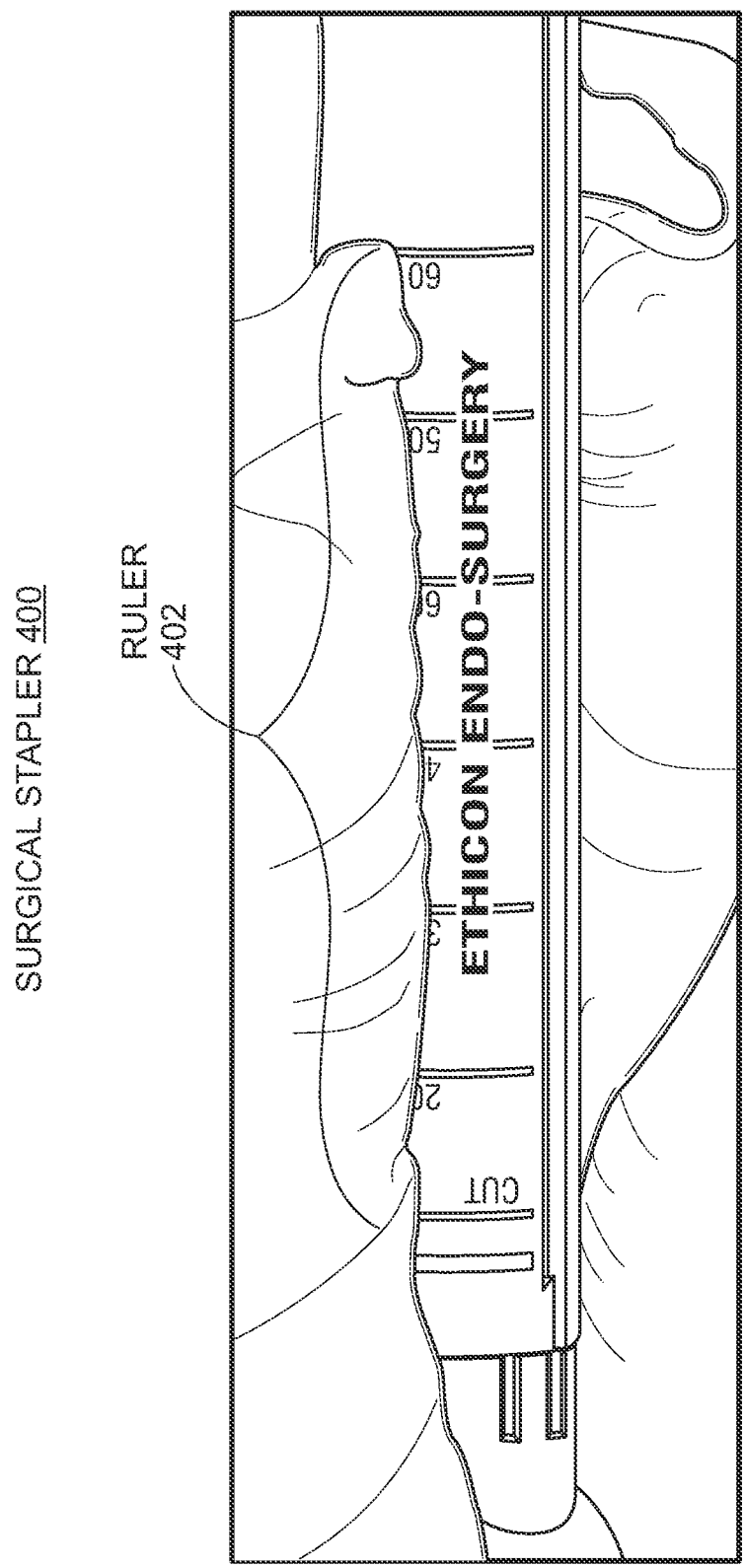
FIG. 4 shows a photographic image depicting a surgical stapler that includes a ruler printed on the cartridge section of the surgical stapler in accordance with some embodiments described herein.

As mentioned above, the counted number of uses/firings of a surgical stapler during a given tool engagement can be used to infer a length of the tissue traversed by the surgical stapler. For example, the approximate length of the tissue that the surgical stapler has traversed during a single engagement can be estimated as the counted number of firings times the length of the cartridge section of the surgical stapler. In some embodiments, the length of the cartridge can be directly extracted from an image of the surgical stapler, which shows a ruler representing the length of the cartridge. For example, FIG. 4 shows a photographic image depicting a surgical stapler 400, which includes a ruler 402 printed on the cartridge section of the surgical stapler in accordance with some embodiments described herein. As shown in FIG. 4, a ruler 402 indicates that for surgical stapler 400, each cartridge is about 6 cm long. Hence, the disclosed tool-usage counting module 108-2 can also include a length estimation function to infer the length of the tissue traversed by the surgical stapler based on the number of firings detected for a given engagement and the extracted length information of the stapler cartridge.

Note that similarly to extracting the cartridge length information from video images of a surgical stapler, other tool-related parameters can also be extracted from video images for an identified surgical tool, such as a surgical stapler. For example, the color of the stapler cartridge/load of a surgical stapler is an important parameter to collect because different colors of the cartridge/load represent different types of staples for different tissue thicknesses. The color of the cartridge/load is also an important parameter during a post-operation summary procedure to summarize what types of stapler load have been used on the patient during the surgical procedure. In some embodiments, the disclosed tool-usage counting module can include an image processing mechanism integrated with process 300 to determine the color of each stapler load for each detected firing of the surgical stapler. The determined color information can be combined with other tool usage information, such as the length of the tissue traversed by the stapler and the number of firings of that surgical stapler extracted from the surgical video. The combined tool usage information can then be used for post-operation analysis.

Figure 5:
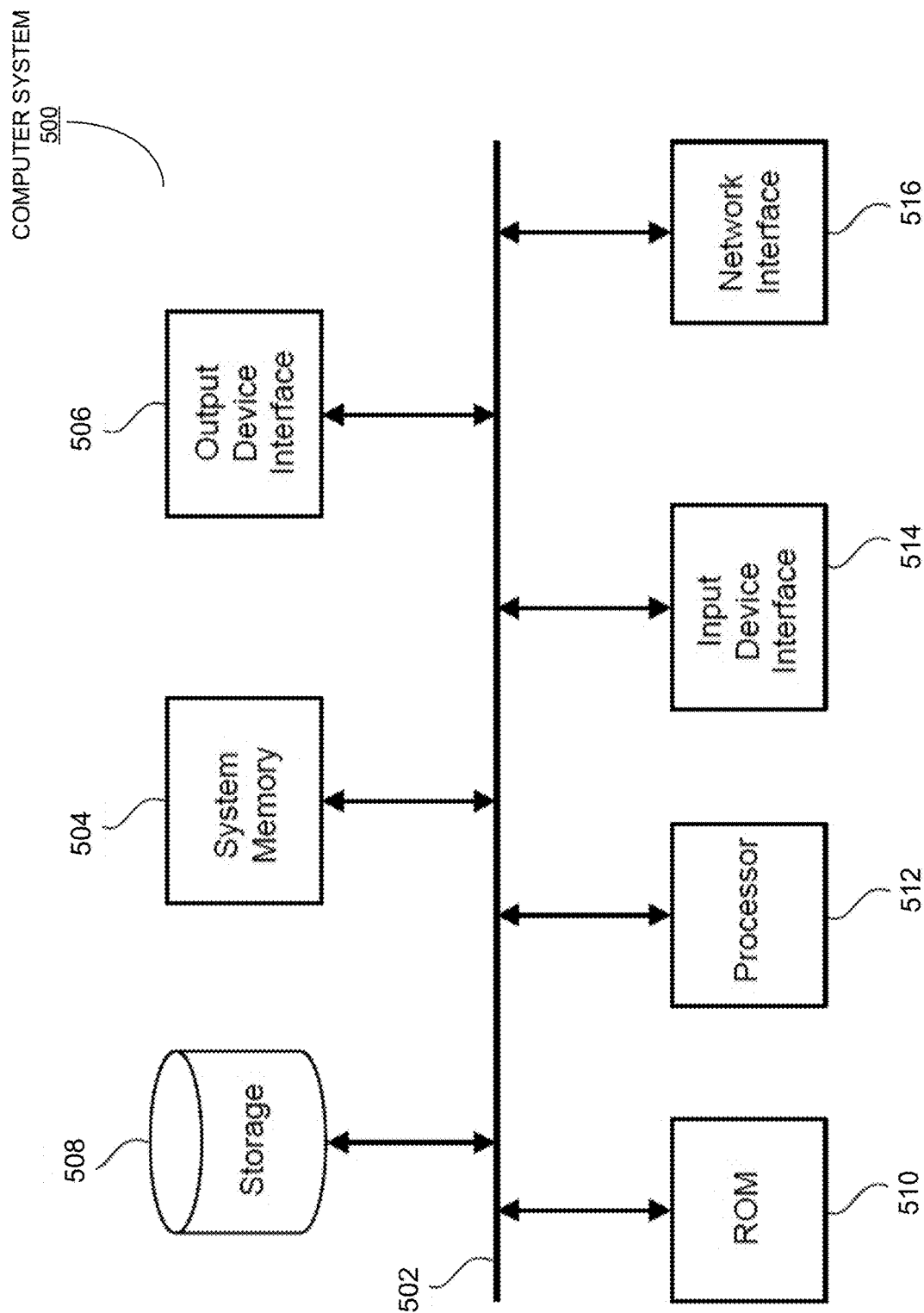
FIG. 5 conceptually illustrates a computer system with which some embodiments of the subject technology can be implemented.

FIG. 5 conceptually illustrates a computer system with which some embodiments of the subject technology can be implemented. Computer system 500 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 500 includes a bus 502, processing unit(s) 512, a system memory 504, a read-only memory (ROM) 510, a permanent storage device 508, an input device interface 514, an output device interface 506, and a network interface 516. In some embodiments, computer system 500 is a part of a robotic surgical system.

Bus 502 collectively represents all system, peripheral, and chipset buses that communicatively connect the numerous internal devices of computer system 500. For instance, bus 502 communicatively connects processing unit(s) 512 with ROM 510, system memory 504, and permanent storage device 508.

From these various memory units, processing unit(s) 512 retrieves instructions to execute and data to process in order to execute various processes described in this patent disclosure, including the above-described processes of detecting which surgical tools have been engaged during a recorded surgical procedure, tracking how many times a limited-use surgical tool has been fired, and evaluating the quality of a newly formed staple line in conjunction with FIGS. 1-3. The processing unit(s) 512 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 512 can be a single processor or a multi-core processor in different implementations.

ROM 510 stores static data and instructions that are needed by processing unit(s) 512 and other modules of the computer system. Permanent storage device 508, on the other hand, is a read-and-write memory device. This device is a non-volatile memory unit that stores instructions and data even when computer system 500 is off. Some implementations of the subject disclosure use a mass-storage device (such as a magnetic or optical disk and its corresponding disk drive) as permanent storage device 508.

Other implementations use a removable storage device (such as a floppy disk, flash drive, and its corresponding disk drive) as permanent storage device 508. Like permanent storage device 508, system memory 504 is a read-and-write memory device. However, unlike storage device 508, system memory 504 is a volatile read-and-write memory, such as a random access memory. System memory 504 stores some of the instructions and data that the processor needs at runtime. In some implementations, various processes described in this patent disclosure, including the processes of detecting which surgical tools have been engaged during a recorded surgical procedure and tracking a number of uses of a limited-use surgical tool in conjunction with FIGS. 1-3, are stored in system memory 504, permanent storage device 508, and/or ROM 510. From these various memory units, processing unit(s) 512 retrieve instructions to execute and data to process in order to execute the processes of some implementations.

Bus 502 also connects to input and output device interfaces 514 and 506. Input device interface 514 enables the user to communicate information to and select commands for the computer system. Input devices used with input device interface 514 include, for example, alphanumeric keyboards and pointing devices (also called "cursor control devices"). Output device interface 506 enables, for example, the display of images generated by computer system 500. Output devices used with output device interface 506 include, for example, printers and display devices, such as cathode ray tubes (CRT) or liquid crystal displays (LCD). Some implementations include devices such as a touchscreen that functions as both input and output devices.

Finally, as shown in FIG. 5, bus 502 also couples computer system 500 to a network (not shown) through a network interface 516. In this manner, the computer can be a part of a network of computers (such as a local area network ("LAN"), a wide area network ("WAN"), an intranet, or a network of networks, such as the Internet. Any or all components of computer system 500 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for automatically tracking usages of robotic surgery tools, the method comprising:
   receiving a surgical video captured during a robotic surgery;
   processing the surgical video to detect a limited-use surgical tool in the surgical video;
   determining whether the detected limited-use surgical tool has been engaged in the robotic surgery, which includes determining if the detected limited-use surgical tool continues to present in the surgical video for at least a predetermined minimum time period by tracking the detected limited-use surgical tool in the surgical video for a predetermined number of consecutive video frames corresponding to the predetermined minimum time period; and
   if so, determining whether the detected limited-use surgical tool has been previously engaged during the robotic surgery:
      if not, incrementing a total-engagement count of the detected limited-use surgical tool;
      otherwise, continuing monitoring the detected limited-use surgical tool in the surgical video.

2. The computer-implemented method of claim 1, wherein processing the surgical video to detect the limited-use surgical tool includes applying a machine-learning model on a set of video images in the surgical video, wherein the machine-learning model is trained to detect and identify a set of surgical tools associated with the robotic surgery.

3. The computer-implemented method of claim 1, wherein in response to determining that the detected limited-use surgical tool has been engaged in the robotic surgery, the method further comprises continuing monitoring the detected limited-use surgical tool in the surgical video.

4. The computer-implemented method of claim 1, wherein prior to determining whether the detected limited-use surgical tool has been engaged in the robotic surgery, the method further comprises, for each type of a set of surgical tool types, determining a minimum time period required to engage the surgical tool type in a surgical procedure.

5. The computer-implemented method of claim 1, wherein if the detected limited-use surgical tool has been previously engaged in the robotic surgery, the method further includes continuing monitoring other surgical tools in the robotic surgery.

6. The computer-implemented method of claim 1, wherein after incrementing the total-engagement count of the detected limited-use surgical tool, the method further includes recording the updated engagement count of the detected limited-use surgical tool for tool inventory purposes.

7. The computer-implemented method of claim 6, wherein if the updated engagement count has reached a maximum number of engagements for the safe and/or effective use of the detected limited-use surgical tool, the method further comprises marking the detected limited-use surgical tool as expired.

8. The computer-implemented method of claim 1, wherein after determining that the detected limited-use surgical tool has been engaged in the robotic surgery, the method further comprises activating a tool-usage counting process to track and record a number of uses of the detected limited-use surgical tool during the tool engagement.

9. The computer-implemented method of claim 8, wherein using the tool-usage counting process to track the number of uses of the detected limited-use surgical tool includes using a second machine-learning model trained to detect an event in the surgical video representing a single use of the detected limited-use surgical tool.

10. The computer-implemented method of claim 9, wherein the detected limited-use surgical tool is a surgical stapler, and wherein the second machine-learning model is trained to detect a single firing of the surgical stapler each time a firing knob of the surgical stapler is pushed from a first position to a second position.

11. The computer-implemented method of claim 9, wherein the detected limited-use surgical tool is an electrocautery tool, and wherein the second machine-learning model is trained to detect a single firing of the electrocautery tool each time a plume of surgical smoke is detected.

12. The computer-implemented method of claim 8, wherein the method further comprises:
   receiving an existing number of total uses of the detected limited-use surgical tool from previous engagements of the detected limited-use surgical tool; and
   updating the total uses of the detected limited-use surgical tool by combining the recorded number of uses during the tool engagement with the existing number of total uses from the previous engagements.

13. The computer-implemented method of claim 12, wherein the method further comprises:
   determining if a maximum number of total uses of the detected limited-use surgical tool has been reached; and
   if so, generating a tool-expiration notification to be communicated to surgical staff.

14. An apparatus for automatically tracking usages of robotic surgery tools, the apparatus comprising:
   one or more processors;

a memory coupled to the one or more processors, the memory storing instructions that, when executed by the one or more processors, cause the apparatus to:
receive a surgical video captured during a robotic surgery;
process the surgical video to detect a limited-use surgical tool in the surgical video;
determine whether the detected limited-use surgical tool has been engaged in the robotic surgery, which includes determining if the detected limited-use surgical tool continues to present in the surgical video for at least a predetermined minimum time period by tracking the detected limited-use surgical tool in the surgical video for a predetermined number of consecutive video frames corresponding to the predetermined minimum time period; and
if so, determine if the detected limited-use surgical tool has been previously-engaged in the robotic surgery:
if not, increment a total-engagement count of the detected limited-use surgical tool;
otherwise, continue monitoring the detected limited-use surgical tool in surgical video.

15. The apparatus of claim 14, wherein the memory further stores instructions that, when executed by the one or more processors, cause the apparatus to activate a tool-usage counting process to track and record a number of uses of the detected limited-use surgical tool during the tool engagement after determining that the detected limited-use surgical tool has been engaged.

16. The apparatus of claim 14, wherein the memory further stores instructions that, when executed by the one or more processors, cause the apparatus to use a second machine-learning model to track the number of uses of the detected limited-use surgical tool, wherein the second machine-learning model is trained to detect an event in the surgical video representing a single use of the detected limited-use surgical tool.

17. The apparatus of claim 14, wherein the memory further stores instructions that, when executed by the one or more processors, cause the apparatus to:
receive an existing number of total uses of the detected limited-use surgical tool from previous engagements of the detected limited-use surgical tool; and
update the total uses of the detected limited-use surgical tool by combining the recorded number of uses during the tool engagement with the existing number of total uses from the previous engagements.

18. The apparatus of claim 15, wherein the memory further stores instructions that, when executed by the one or more processors, cause the apparatus to:
determine if a maximum number of total uses of the detected limited-use surgical tool has been reached; and
if so, generate a tool-expiration notification to be communicated to surgical staff.

19. A robotic surgical system, comprising:
one or more surgical tools each coupled to a respective robotic arm;
an endoscope configured to capture surgical videos; and
a controller coupled to each robotic arm and the endoscope and configured to:
receive a surgical video captured by the endoscope during a robotic surgery;
process the surgical video to detect a limited-use surgical tool in the surgical video;
determine whether the detected limited-use surgical tool has been engaged in the robotic surgery, which includes determining if the detected limited-use surgical tool continues to present in the surgical video for at least a predetermined minimum time period by tracking the detected limited-use surgical tool in the surgical video for a predetermined number of consecutive video frames corresponding to the predetermined minimum time period; and
if so, determine whether the detected limited-use surgical tool has been previously engaged during the robotic surgery:
if not, increment a total-engagement count of the detected limited-use surgical tool;
otherwise, continue monitoring the detected limited-use surgical tool in the surgical video.

20. The robotic surgical system of claim 19, wherein the controller is further configured to:
detect that the total-engagement count has reached a maximum number of engagements for the safe and/or effective use of the detected limited-use surgical tool; and
mark the detected limited-use surgical tool as expired and update a status of the detected surgical tool for tool inventory purposes.

* * * * *